United States Patent [19]

McKenna

[11] Patent Number: 4,834,728
[45] Date of Patent: May 30, 1989

[54] EYE DROP DISPENSER APPARATUS

[76] Inventor: Bill McKenna, 2000 W. 18th, Sioux City, Iowa 51103

[21] Appl. No.: 138,061

[22] Filed: Dec. 28, 1987

[51] Int. Cl.⁴ .......................................... A61H 33/04
[52] U.S. Cl. .................................... 604/301; 222/192; 222/566
[58] Field of Search ............... 222/575, 566, 460, 192; 604/295–302

[56] References Cited

U.S. PATENT DOCUMENTS

| | | | |
|---|---|---|---|
| 1,603,727 | 10/1926 | Vilas | 604/298 |
| 2,283,668 | 5/1942 | Demsey | 604/301 |
| 2,516,818 | 7/1950 | West | 604/298 |
| 2,585,264 | 2/1952 | Mock | 604/301 |
| 2,626,606 | 1/1953 | Campbell | 604/301 |
| 2,898,911 | 8/1959 | Taylor | 604/301 |
| 3,016,898 | 1/1962 | Erwin | 604/298 |
| 3,170,462 | 2/1965 | Hall | 604/298 X |
| 3,279,466 | 10/1966 | Mings | 604/302 |
| 4,175,704 | 11/1979 | Cohen | 604/295 X |
| 4,733,802 | 3/1988 | Sheldon | 604/302 X |

FOREIGN PATENT DOCUMENTS

| | | | |
|---|---|---|---|
| 0647481 | 10/1962 | Italy | 604/302 |
| 1280014 | 7/1972 | United Kingdom | 604/302 |
| 2142829A | 1/1985 | United Kingdom | 604/295 |

Primary Examiner—Joseph J. Rolla
Assistant Examiner—Stephen B. Parker
Attorney, Agent, or Firm—Leon Gilden

[57] ABSTRACT

A selectively securable eye drop dispenser apparatus as set forth wherein a replacement cap for use of the conventional eye drop dispensers has formed a threaded cylindrical portion for securement to the aforenoted conventional eye drop bottle including an orifice portion directed to an eye cup portion for operative associated with a human eye. The eye cup portion is formed of a flexible plastic-like material for enabling conformity to an associated human eye wherein the cylindrical threaded portion is formed of relatively stiff plastic-like material for maintaining desired registry and orientation of the associated orifice portion with the eye drop bottle.

1 Claim, 2 Drawing Sheets

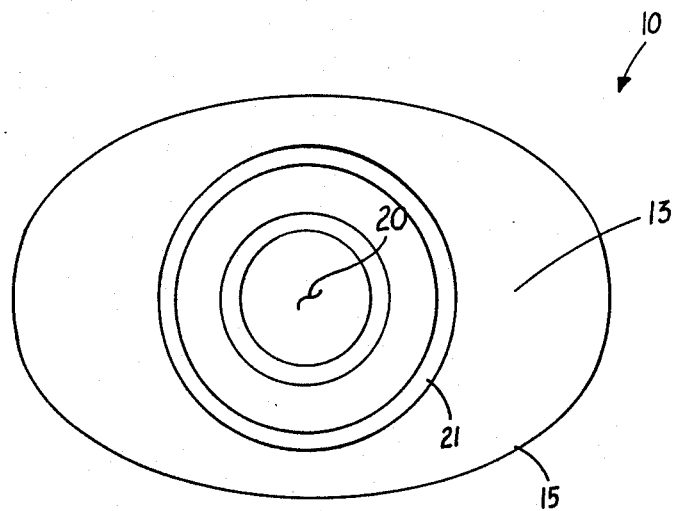
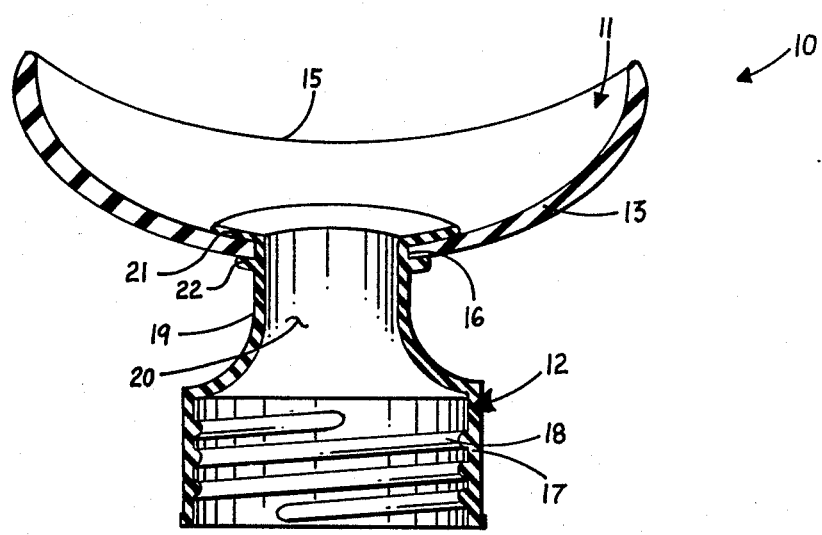

EYE DROP DISPENSER APPARATUS

BACKGROUND OF THE INVENTION

1. Field of the Invention

The present invention relates to eye drop dispenser apparatus and more particularly pertains to a new and improved eye drop dispenser apparatus which includes an eye drop cup associated with an eye drop bottle registering base formed of varying durometers to enable the eye drop cup to conform to a human eye and the eye drop base to securely associate with an eye drop dispenser.

2. Description of the Prior Art

The use of eye drop directing apparatus and the like is well known in the prior art. As may be appreciated, these devices have normally been configured and changed for conformity with an average human eye in mind. Understandably, human eyes will vary as does the general human physiology and accordingly, the ability for conventional eye drop directing constructions of the past has been somewhat limited. Furthermore, when conventional eye droppers are utilized for application of medicine and such the self-application of such drops by individuals is sometimes cumbersome and difficult due to the proximity of the eye dropper to the target eye. In this connection, there have been several attempts to develop eye drop apparatus and the like which may be easily and effectively utilized when desired. For example, U.S. Pat. No. 3,260,425 to Moran sets forth a self-sealing dispenser apparatus with a flexible bellows-like integral cap portion to plug the flow of fluid from an associated container. A conventional spout arrangement is provided by the Moran patent.

U.S. Pat. No. 3,235,146 to Parish, Jr. et al. sets forth a spout member that includes a portion movable to a fully retracted and stored position and a fully extended pouring position for selective use. A flared outer rim is associated with the spout arrangement for retracted support within the container.

U.S. Pat. No. Des. 249,647 to Goodall, U.S. Pat. No. Des. 241,624 to Trott, U.S. Pat. No. Des. 198,598 to Milenkevich, and U.S. Pat. No. Des. 133,978 to Johnson are illustrative of known prior art dispenser arrangements associatable with containers for varying needs.

As such, it may be appreciated that there is a continuing need for a new and improved eye drop dispenser apparatus which addresses both the problem of positioning and directing of eye drop fluids associated with varying eye drop dispensing arragements and in this respect, the present invention substantially fulfills this need.

SUMMARY OF THE INVENTION

In view of the foregoing disadvantages inherent in the known types of eye drop dispenser apparatus now present in the prior art, the present invention provides an eye drop dispenser apparatus which includes an eye associating cup formed of flexible plastic-like material in integral association with a rigid plastic-like base threadedly securable to an associated eye drop dispenser bottle. As such, the general purpose of the present invention, which will be described subsequently in greater detail, is to provide a new and improved eye drop dispenser apparatus which has all the advantages of the prior art eye drop dispenser apparatus and none of the disadvantages.

To attain this, the present invention comprises a base portion formed as a threadedly securable cylindrical portion threadedly registrable with an associated eye drop dispenser bottle tapering to an orifice portion for directing such fluid to a human eye with a relatively flexible eye cup integrally secured to said orifice portion and registrable with the human eye for a more precise directing of eye drop fluids thereto.

My invention resides not in any one of these features per se, but rather in the particular combination of all of them herein disclosed and claimed and it is distinguished from the prior art in this particular combination of all of its structures for the functions specified.

There has thus been outline, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is of enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved eye drop dispenser apparatus which has all the advantages of the prior art eye drop dispenser apparatus and none of the disadvantages.

It is another object of the present invention to provide a new and improved eye drop dispenser apparatus which may be easily and efficiently manufactured and marketed.

It is a further object of the present invention to provide a new and improved eye drop dispenser apparatus which is of a durable and reliable construction.

An even further object of the present invention is to provide a new and improved eye drop dispenser apparatus which is susceptible of a low cost of manufacture with regard to both materials and labor, and which accordingly is then susceptible of low prices of sale to the consuming public, thereby making such eye drop dispenser apparatus economically available to the buying public.

Still yet another object of the present invention is to provide a new and improved eye drop dispenser apparatus which provides in the apparatuses and methods of the prior art some of the advantages thereof, while simultaneously overcoming some of the disadvantages normally associated therewith.

Still another object of the present invention is to provide a new and improved eye drop dispenser apparatus formed of a relatively flexible eye drop cup integrally secured to a relatively rigid eye drop bottle attachment portion.

Yet another object of the present invention is to provide a new and improved eye drop dispenser apparatus wherein a threadedly securable base portion tapers to an eye drop directing orifice portion associated integrally with a flexible eye drop cup for alignment of the eye drop dispenser bottle with a target human eye.

these together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic plan view of the instant invention as viewed from the base portion thereof.

FIG. 4 is an orthographic side view of the instant invention taken along the lines 4—4 of FIG. 1 in the direction indicated by the arrows.

DESCRIPTION OF THE PREFERRED EMBODIMENT

Figure 1:
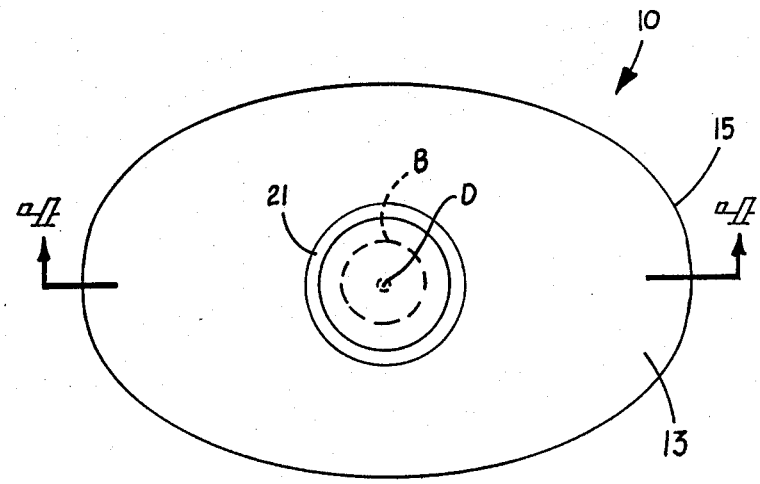
FIG. 1 is a top orthographic view of the instant invention.

With reference now to the drawings, and in particular to FIGS. 1 to 4 thereof, a new and improved eye drop dispenser apparatus embodying the principles and concepts of the present invention and generally designated by the reference numeral 10 will be described.

More specifically, it will be noted that the eye drop dispenser apparatus 10 essentially comprises an eye cup portion 11 associated with a base portion 12. As best illustrated in FIG. 4, for example, eye cup portion 11 is formed of a relatively flexible plastic-like material of a more flexible and hence lower durometer rating than the associated base portion 12. The eye cup portion 11 is formed with a concave curvilinear support 13 terminating in a ellipsoidal periphery 15 providing relative conformity to the human and anatomical curvature about a human eye. The relatively flexible plastic-like material forming the eye cup portion 11 enables registration about a human eye over a wide variety of anatomical variances. The concave curvilinear support 13 has formed medially therethrough an opening defined by a periphery 16.

Figure 2:
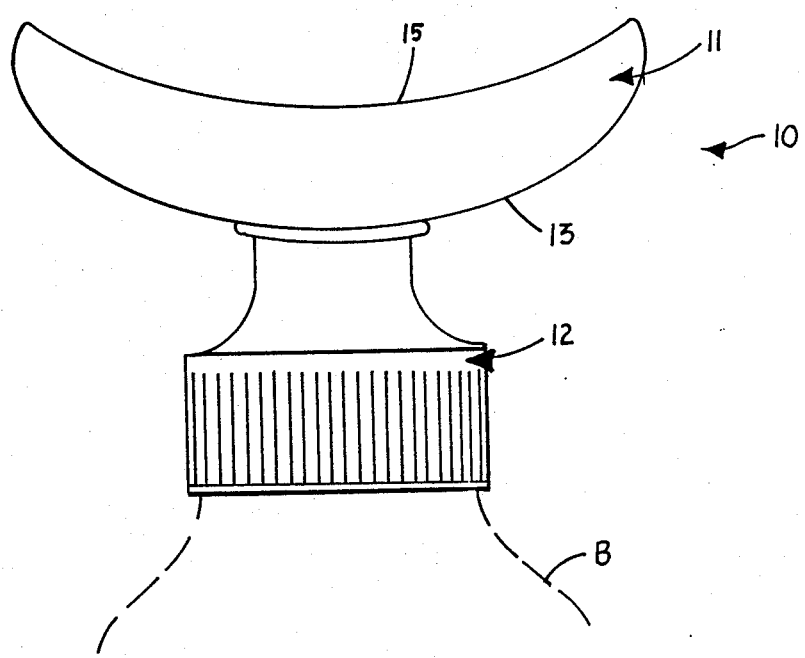
FIG. 2 is a side orthographic view taken in elevation of the instant invention in association with an eye drop dispenser bottle.

The base portion 12 comprises a lower cylindrical bottle support portion 17 formed with internal threads 18 for threadedly engaging an eye dropper bottle "B" of conventional flexible construction that is utilized to dispense various eye fluids and medications, as illustrated in FIG. 2. The cylindrical bottle support portion 17 terminates into an orifice defining neck 19 for engagement with the terminal periphery 16 by means of a generally "U" shaped engagement portion defined by an overlying circumferential lip 21 of a width greater than that of an underlying lip 22 for both sealing and securement of the eye cup portion 11. The variation in width of overlying lip 21 to lower lying 22 effects and added degreee of flexibility enabling the eye cup 11 to associate with a human eye. FIG. 1 illustrates the dispenser bottle "B" and an associated central dispenser opening "D" and the alignment through the orifice neck portion 19 directing eye drop fluid therethrough.

As to the manner of usage and operation of the present invention, the same should be apparent from the above description. Accordingly, no further discussion relative to the manner of usage and operation will be provided.

With respect to the above description then, it is to b e realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An eye drop dispenser apparatus for alignment of an eye fluid dispenser container with a human eye, comprising, a base portion means for engagement with a container including orifice means for directing fluid from said container therethrough, and an eye cup means integrally associated with said base portion means for registration with a human eye for enabling alignment of said container with said eye, and wherein said base portion means includes internal threads for threadedly engaging said container, and wherein said orifice means includes a tapered opening integrally formed with said base portion means of a lesser diameter than said threaded portion of said base portion means, and wherein said eye cup means and said base portion means are both formed of polymeric materials but wherein said eye cup means is of a more flexible polymeric material than said base portion means, and wherein said eye cup means is formed of a material of lesser hardness than said base portion means, and wherein said base portion means is secured to said eye cup means by a "U" shaped engagement portion, and wherein said "U" shaped engagement portion is formed of an overlying circumferential lip of greater width than a lower lip for engagement about a central opening in said eye cup means enabling enhanced flexibility of said eye cup means, and wherein said eye cup means is formed as a concave curvilinear support portion terminating in an ellipsoidal periphery.

* * * * *